United States Patent [19]
Rubin et al.

[11] Patent Number: 5,637,479
[45] Date of Patent: Jun. 10, 1997

[54] METHOD OF MODULATING DNA BINDING ACTIVITY OF RECOMBINANT α-1 ANTICHYMOTRYPSIN AND OTHER SERINE PROTEASE INHIBITORS

[75] Inventors: Harvey Rubin, Philadelphia; Barry Cooperman, Penn Valley, both of Pa.

[73] Assignee: The Trustees of the University of Pennsylvania, Philadelphia, Pa.

[21] Appl. No.: 435,480

[22] Filed: May 5, 1995

Related U.S. Application Data

[63] Continuation-in-part of Ser. No. 276,936, Jul. 19, 1994, Pat. No. 5,612,194, which is a continuation-in-part of Ser. No. 229,286, Apr. 18, 1994, abandoned, which is a continuation-in-part of Ser. No. 221,078, Mar. 31, 1994, Ser. No. 221,171, Mar. 31, 1994, and Ser. No. 5,908, Jan. 15, 1993, Pat. No. 5,367,064, which is a division of Ser. No. 735,335, Jul. 24, 1991, Pat. No. 5,252,725, which is a division of Ser. No. 370,704, Jun. 23, 1989, Pat. No. 5,079,336, said Ser. No. 221,078, is a continuation-in-part of Ser. No. 5,908.

[51] Int. Cl.$^6$ .......................... C07K 14/435; C07K 14/81; C12N 15/15

[52] U.S. Cl. ...................... 435/69.2; 435/172.3; 530/350; 530/395; 536/23.5

[58] Field of Search ................................ 435/69.2, 172.3; 530/350, 395; 536/23.5

[56] References Cited

PUBLICATIONS

Abraham et al., "Immunochemical Identification of the Serine Protease Inhibitor $\alpha_1$–Antichymotrypsin in the Brain Amyloid Deposits of Alzheimer's Disease," *Cell* 1988, 52, 487–501, Baird et al., "$O_2$ Metabolites and Neutrophil Elastase Synergistically cause Edematous Inhury in Isolatd Rat Lungs," *Physiol.* 1986, 61, 2224–2229.

Baumann et al., "Crystal Structure of Cleaved Human $\alpha_1$–Antichymotrypsin at 2.1 Å Resolution and Its Comparison with Other Serpins," *J. Mol. Biol.* 1991, 218, 595–606.

Buck et al., "Protein Estimation by the Product of Integrated Peak Area and Flow Rate," *Anal. Biochem.* 1989, 182, 001–005.

Chandra et al., "Sequence Homology between Human $\alpha_1$–Antichymotrypsin, α1–Antitrypsin, and Antithrombin III," *Biochemistry* 1983, 22, 5055–5060.

Emerson et al., "Protection Against Disseminated Intravascular Coagulation and Death by Antithrombin–III in the *Echerichis coli* Endotexemic Rat," *Circ. Shock* 1987, 21, 1.

Eriksson et al., "Familial $\alpha_1$Antichymotrypsin Deficiency," *Acta Med Scand* 1986, 220, 447–453.

Garner, M. and Revzon, A., "A Gel Electrophoresis Method for Quantifying the Binding of Proteins to Specific DNA Regions: Application to Components of the *Escherichia coli* Lactose Operon Regulatory System," *Nucleic Acids Res.* 1981, 9, 3047–3060.

Gennaro, Alfonso, ed., *Remington's Pharmaceutical Sciences*, 18th edition, 1990, Mack Publishing Co., Easton, PA.

Gross, E. et al, "Nonenzymatic Cleavage of Peptide Bonds: the Methionine Residues in Bovine Pancreatic Ribonuclease," *J. Biol. Chem.* 1962, 237, 1856–1860.

Hill et al., "Plasma Protease Inhibitors in Mouse and Man," *Nature* 1984, 311, 175–177.

Huber, R. et al., "Implications of the Three–Dimentional Structure of $\alpha_1$–Antitrypsin for Structure and Function of Serpins," *Biochemistry* 1989, 28, 8951–8966.

Katsunama et al., "Purification of a Serum DNA Protein(64DP) with a Molecule Weight of 64,000 and its Diagnostic Significance in Malegnant Diseases," *Biochem. Biophys. Res. Commun.* 1980, 93, 552–557.

Kilpatrick et al., "Inhibition of Human Neutrophil Superoxide Generation by $\alpha_1$–Antitrypsin," *J. Immunol.* 1991, 146, 2388.

Lindmark, B.E. et al., "Plasma $\alpha_1$–Antichymotrypsin in Liver Disease," *Clin. Chim. Acta* 1985m 152, 261–269.

Maniatis et al. "Molecular Cloning: A Laboratory Manual", 1982, Cold Spring Harbor Laboratory Press, Cold Spring Harbor, NY.

Nagai et al., "Administration of α–1–Proteinase Inhibitor Ameliorates Bleomycine–induced Pulmonary Fibrosis in Hamsters," *Am. Rev. Resp. Dis.* 1992, 145, 651.

Poller, W. et al., "A Leucine–to–Proline Substitution Causes a Defective $\alpha_1$–Antichymotrypsin Allele Associated with Familal Obstructive Lung Disease," *Genomics* 1993, 17, 740–743.

Redens et al., "Synergistic Protection from Lung Damage by Combining Antithrombin–III and α1–Proienase Inhibitor in the *E. coli* Endotixiemic Sheep Pulmonary Dysfunction Model," *Circ. Shock* 1988, 26, 15.

Rosengren et al., "Neutrophil–mediated Vascular Leakage is not Suppresed by Leukocyte Elastase Inhibitors," *Am. J. Physiol.* 1990, 259, H1288.

Rubin et al., "Cloning, Expression, Purification and Biological Activity of Recombinant Native and Variant Human $\alpha_1$–Antichymotrypsins," *J. Biol. Chem.* 1990, 265, 1199–1207.

Rubin et al., "Conversion of $\alpha_1$–Antichymotrypsin into a Human Neutrophil Elastase Inhibitor," *Biochemistry* 1994, 33, 7627–7633.

Schagger, H. et al., "Tricine–Sodium Dodecyl Sulfate–Polyacrylamide Gell Electrophoresis for the Separation of Protein in the Range from 1 to 100 kDa," *Anal. Biochem.* 1987, 166, 368–379.

Schecter et al., "Reaction of Human Chymase with Reactive Site Variants of $\alpha_1$–Antichymotrypsin," *J. Biol. Chem.* 1993, 268, 23626–23633.

(List continued on next page.)

*Primary Examiner*—Dian C. Jacobson
*Attorney, Agent, or Firm*—Law Offices of Jane Massey Licata

[57] ABSTRACT

A method of producing a recombinant ACT analogs having modulated DNA binding capability is provided. Recombinant ACT analogs having modulated DNA binding capability are also provided.

2 Claims, No Drawings

PUBLICATIONS

Suzuki et al., "Molecular Cloning and Sequence Analysis of Full–Length cDNA Coding for Mouse Contrapsin," *J. Biochem.* 1990, 108, 344–346.

Takada et al., "Analysis of the Tissur and Cellular Localization of $\alpha_1$–Antichymotrypsin by an Immunohistochemical Technique," *Gann* 1982, 73, 742–747.

Takada et al., "Incorporation of $\alpha_1$–Antichymotrypsin into Carcinoma Cell Neclei of Human Stomach Adenocarcimoma Transplanted into Nude Mice," *Cancer Res.* 1986, 46, 3688–3691.

Tsuda et al., "Effect of $\alpha_1$–Antichymotrypsin on DNA Synthesis in Permeabilized Human Cells," *Biochem. Biophys. Res. Commun.* 1987, 144, 409–414.

Tsuda et al., "Inhibition of Human DNA Polymerase $\alpha$ by $\alpha_1$–Antichymotrypsin," *Cancer Res.* 1986, 46, 6139–6142.

Takada et al., "Effect of $\alpha_1$–Antichymotrypsin on Activity of DNA Primase Isolated From Human Stomach Adenocarcinoma Cells," *Biochem. Int.* 1988, 16, 949–954.

Travis, J. et al., "Human Plasma Proteinase Inhibitors," *Annu. Rev. Biochem.* 1983, 52, 655–709.

Wei, A. et al., "Crystal Structure of an Uncleaved Serpin Reveas the Comformation of an Inhibitory Reactive Loop," *Struct. Bio.* 1994, 1,4, 251–258.

SEQUENCE LISTING ( 1 ) GENERAL INFORMATION:

( i i i ) NUMBER OF SEQUENCES: 11

( 2 ) INFORMATION FOR SEQ ID NO: 1:

( i ) SEQUENCE CHARACTERISTICS:
( A ) LENGTH: 36
( B ) TYPE: Nucleic Acid
( C ) STRANDEDNESS: Single
( D ) TOPOLOGY: Linear ( i v ) ANTI-SENSE: No ( x i ) SEQUENCE DESCRIPTION: SEQ ID NO: 1:

GCACCATTAC CCACTTTGTC TTGCTCAAGT AGAACC 36

( 2 ) INFORMATION FOR SEQ ID NO: 2:

( i ) SEQUENCE CHARACTERISTICS:
( A ) LENGTH: 36
( B ) TYPE: Nucleic Acid
( C ) STRANDEDNESS: Single
( D ) TOPOLOGY: Linear ( i v ) ANTI-SENSE: No ( x i ) SEQUENCE DESCRIPTION: SEQ ID NO: 2:

GCACCATTAC CCACTCTTCC TCGCTCAAGT AGAACC 36

( 2 ) INFORMATION FOR SEQ ID NO: 3:

( i ) SEQUENCE CHARACTERISTICS:
( A ) LENGTH: 36
( B ) TYPE: Nucleic Acid
( C ) STRANDEDNESS: Single
( D ) TOPOLOGY: Linear ( i v ) ANTI-SENSE: No ( x i ) SEQUENCE DESCRIPTION: SEQ ID NO: 3:

GCACCATTAC CCACGTTGTC TTGCTCAAGT AGAACC 36

( 2 ) INFORMATION FOR SEQ ID NO: 4:

( i ) SEQUENCE CHARACTERISTICS:
( A ) LENGTH: 36
( B ) TYPE: Nucleic Acid
( C ) STRANDEDNESS: Single
( D ) TOPOLOGY: Linear ( i v ) ANTI-SENSE: No ( x i ) SEQUENCE DESCRIPTION: SEQ ID NO: 4:

GCACCATTAC CCACGTTGTC GTGCTCAAGT AGAACC 36

( 2 ) INFORMATION FOR SEQ ID NO: 5:

( i ) SEQUENCE CHARACTERISTICS:
( A ) LENGTH: 12
( B ) TYPE: Amino Acid
( D ) TOPOLOGY: Linear ( x i ) SEQUENCE DESCRIPTION: SEQ ID NO: 5:

Met Gly Arg Asp Leu Cys His Pro Asn Ser Pro Leu
1               5                   10

( 2 ) INFORMATION FOR SEQ ID NO: 6:

( i ) SEQUENCE CHARACTERISTICS:
        ( A ) LENGTH: 21
        ( B ) TYPE: Nucleic Acid
        ( C ) STRANDEDNESS: Single
        ( D ) TOPOLOGY: Linear ( i v ) ANTI-SENSE: No ( x i ) SEQUENCE DESCRIPTION: SEQ ID NO: 6:

ATGGCTAGCA ACAGCCCACT T                                       21

( 2 ) INFORMATION FOR SEQ ID NO: 7:

( i ) SEQUENCE CHARACTERISTICS:
        ( A ) LENGTH: 47
        ( B ) TYPE: Nucleic Acid
        ( C ) STRANDEDNESS: Single
        ( D ) TOPOLOGY: Linear ( i v ) ANTI-SENSE: No ( x i ) SEQUENCE DESCRIPTION: SEQ ID NO: 7:

TGGCTAGCCT AGGCTTGCGT GGGATTGGTG ACTGTGCTCA TGAAGAA            47

( 2 ) INFORMATION FOR SEQ ID NO: 8:

( i ) SEQUENCE CHARACTERISTICS:
        ( A ) LENGTH: 7
        ( B ) TYPE: Amino Acid
        ( D ) TOPOLOGY: Linear ( x i ) SEQUENCE DESCRIPTION: SEQ ID NO: 8:

Met Asp Ser Asn Ser Pro Leu
1                   5

( 2 ) INFORMATION FOR SEQ ID NO: 9:

( i ) SEQUENCE CHARACTERISTICS:
        ( A ) LENGTH: 6
        ( B ) TYPE: Amino Acid
        ( D ) TOPOLOGY: Linear ( x i ) SEQUENCE DESCRIPTION: SEQ ID NO: 9:

Leu Thr Asp Ala Asp Phe
1                 5

( 2 ) INFORMATION FOR SEQ ID NO: 10:

( i ) SEQUENCE CHARACTERISTICS:
        ( A ) LENGTH: 5
        ( B ) TYPE: Nucleic Acid
        ( C ) STRANDEDNESS: Single
        ( D ) TOPOLOGY: Linear ( i v ) ANTI-SENSE: No ( x i ) SEQUENCE DESCRIPTION: SEQ ID NO: 10:

AGGTT                                                              5

( 2 ) INFORMATION FOR SEQ ID NO: 11:

( i ) SEQUENCE CHARACTERISTICS:
        ( A ) LENGTH: 39
        ( B ) TYPE: Nucleic Acid
        ( C ) STRANDEDNESS: Single
        ( D ) TOPOLOGY: Linear -continued ( i v ) ANTI-SENSE: No ( x i ) SEQUENCE DESCRIPTION: SEQ ID NO: 11:

AGGTTTGGGA AATGCCAGGA CAACCAATGT TCTGTTCTA 39

METHOD OF MODULATING DNA BINDING ACTIVITY OF RECOMBINANT α-1 ANTICHYMOTRYPSIN AND OTHER SERINE PROTEASE INHIBITORS

This invention was made in the course of research sponsored in part by the National Institutes of Health. The U.S. Government may have certain rights in this invention.

This application is a continuation-in-part of 08/276,936, filed Jul. 19, 1994, now allowed, U.S. Pat. No. 5,612,194; which is a CIP of 08/229,286, filed Apr. 18, 1994, now abandoned; which is a CIP of 08/221,078, filed Mar. 31,1994 and a CIP of 08/221,171, filed Mar. 31, 1994; both 08/221,078 and 08/221,171 are a CIP of 08/005,908, filed Jan. 15, 1993, U.S. Pat. No. 5,367,064; which is a divisional of 07/735,335, filed Jul. 24, 1991, U.S. Pat. No. 5,252,725; which is a divisional of 07/370,704, filed Jun. 23, 1989, U.S. Pat. No. 5,079,336.

BACKGROUND OF THE INVENTION

Serine protease inhibitors or "serpins" are a superfamily of inhibitors involved in the mediation of a variety of biological processes essential to survival of a host. Members of the serpin family play a role in a great number of biological processes including, but not limited to, inflammation, fertilization, tumor migration, neurotropism, and heat shock. Maspin was recently identified and characterized as a protective serpin normally present in mammary epithelium but absent from most mammary carcinoma cell lines. Serpins are found in plants, prokaryotes, insects and animals. Natural mutations and modifications of serpins are correlated with a number of serious disease states. Serpin dysfunction is associated with lung, liver and blood coagulation diseases such as emphysema, liver cirrhosis, thrombosis and pulmonary embolism.

The interaction of serpins with endogenous and microbial proteases produces a spectrum of molecular species, each of which are components of a highly evolutionarily conserved homeostatic mechanism that operates to maintain concentrations of intact, active serpins essential to a host's survival. For example, the serpin-protease complex and the hydrolyzed, inactive form of the intact serpin stimulate the production of interleukin-6, signaling hepatocytes to increase synthesis of the acute phase proteins including a subpopulation of the serpin superfamily of proteins. While serpin-enzyme complexes are rapidly cleared from the circulation, cleaved and intact forms of these complexes can accumulate in local areas of inflammation. This accumulation establishes a complex microenvironment of chemoattractants and inhibitors of chemotaxis as well as activators and inhibitors of neutrophil degranulation, leukotrienes, platelet activating factor (PAF), and superoxide production. The extreme virulence of several pox viruses has been attributed in part to a serpin whose target is cysteine proteinase ICE, the interleukin 1-β converting enzyme.

Through various animal models, it has been demonstrated that uncontrolled serine protease activity is a major mechanism of lung injury and that an appropriate serpin response controls the degree of the injury. For example, antithrombin III (ATIII) in combination with α-1-protease inhibitor (α1P1), protected sheep from endotoxin-induced lung injury where the individual serpins were not as effective as the combination. Redens et al., *Circ. Shock* 1988, 26, 15. Redens et al. also showed that ATIII protects against the development of disseminated intravascular coagulation in endotoxemic rats. Emerson et al., *Circ. Shock* 1987, 21, 1. A scavenger of $H_2O_2$ and a chloromethyl ketone inhibitor of elastase blocked reactive oxygen potentiation of neutrophil elastase-mediated acute edematous lung injury in a rat and α1P1 diminished bleomycin-mediated pulmonary inflammation as well as subsequent fibrosis. Baird et al., *Physiol.* 1986, 61, 2224 and Nagai et al., *Am. Rev. Resp. Dis.* 1992, 145, 651. In another system, however, neutrophil elastase inhibitors, Eglin C and a low molecular weight compound L 658,758, failed to inhibit leukotriene B4-induced-neutrophil-mediated adherence, diapedesis or vascular leakage. Rosengren et al., *Am J. Physiol.* 1990, 259, H1288. As shown by these studies, inhibitors of proteolytic enzymes administered therapeutically can limit the molecular and cellular mechanism of inflammation and reduce tissue damage.

There are two subfamilies within the serpin superfamily. One family contains proteins for which no cognate serine proteases have yet been identified. Examples of proteins in this subfamily include ovalbumin, angiotensinogen and steroid binding globulins. The second family contains members for which at least one serine protease can be found as an inhibitory target. The subfamily of serpins that inhibit serine proteases have characteristic properties that define the activity of the inhibitor, i.e., second order rate constants for inhibition of their cognate enzyme range between $10^2$ and $10^7$ $M^{-1}s^{-1}$; the enzyme-inhibitor complex is stable under certain conditions and can be detected as a species with a molecular weight greater than the individual components in SDS polyacrylamide gels; and, a large conformational change occurs upon cleavage of the sessile bond in the reactive center leading to increased thermal stability of the protein. An example of a serpin in this subfamily is α1-antichymotrypsin (ACT), an inhibitor of chymotrypsin (Chtr). ACT is synthesized predominantly by the liver and is one of the acute phase reactants with levels rising rapidly to more than 5 fold in response to a wide variety of injuries including surgery, acute myocardial infarctions, burns, autoimmune diseases, malignancies, infections and liver allograft rejection. ACT has also been linked with the plasticity of the nervous system and associated with beta amyloid deposits in Alzheimer's disease, in aging brain, Down's syndrome and in the Dutch variant of hereditary cerebral hemorrhage with amyloidosis. It has been demonstrated that both native ACT and recombinant ACT (rACT) inhibit superoxide generation by human neutrophils in suspension.

ACT appears to be unique among serpins in its ability to bind to DNA. Katsunama et al., *Biochem. Biophys. Res. Commun.* 1980, 93, 552. This property is also retained by the nonglycosylated recombinant form, rACT, expressed in *E. coli*. Rubin et al., *J. Biol. Chem.* 1990, 265, 1199. ACT, derived from serum, is found in carcinoma cell nuclei (Takada et al., *Gann* 1982, 73, 742; Takada et al., *Cancer Res.* 1986, 46, 3688), as well as in the nuclei of non-malignant cells, including those from human neural tissue (Abraham et al., *Cell* 1988, 52, 487). ACT has been shown to inhibit DNA synthesis in permeabilized human carcinoma cells. Tsuda et al., *Biochem. Biophys. Res. Commun.* 1987, 144, 409. It has been suggested that this inhibition is a result of ACT inhibition of DNA polymerase alpha (Tsuda et al., *Cancer Res.* 1986, 46, 6139) and/or of DNA primase (Takada et al., *Biochem Int.* 1988, 16, 949). ACT also inhibits natural killer cells, which are responsible for tumor lysis, and it has been suggested that ACT present in the nucleus may act as a protective agent for tumor cells. Travis, J. and Salvesen, G. S., *Annu. Rev. Biochem.* 1983, 52, 655. It is also believed that ACT may modulate the level of chymotrypsin-like enzyme activity found in chromatin. Travis, J. and Salvesen, G. S., *Annu. Rev. Biochem.* 1983, 52, 655. ACT may also play a role in cell death and apoptosis.

Using site-directed mutagenesis and chemical modification, specific regions of the rACT amino acid sequence have been identified which are important elements for DNA binding of ACT.

SUMMARY OF THE INVENTION

An object of the present invention is to provide a method of producing recombinant ACT analogs which are capable of effectively modulating serine protease activity but which have modulated DNA binding capability.

Another object of the present invention is to provide recombinant ACT analogs which are capable of effectively modulating serine protease activity but which have modulated DNA binding capability.

DETAILED DESCRIPTION OF THE INVENTION

The human serum serine protease inhibitor (serpin) α1-antichymotrypsin (ACT) has the ability to bind to double stranded DNA (dsDNA). ACT has been localized in the nuclei of certain malignant and non-malignant cells and has been reported to inhibit DNA polymerase alpha, DNA synthesis in permeabilized human carcinoma cells, and poly-C-dependent primase, and to stimulate poly dT dependent primase. Comparison of the primary structure of ACT with those of well-studied serpins such as antithrombin III, α1-P1, or C1- inhibitor (Huber, R. and Carrell, R. W., *Biochemistry* 1989, 28, 8951) showed it to contain a stretch of three consecutive lysines (residues 210–212) not present in the others. The X-ray crystal structures of cleaved ACT (Baumann et al., *J. Mol. Biol.* 1991, 218, 595) and an intact rACT variant (Wei et al., *Nature Structural Biology* 1994, 1, 250) show these three lysines to fall in a solvent-exposed loop.

It has now been found that lysine residues within two short regions of rACT are important for DNA binding. rACT has two elements, a stretch of lysines (residues 210–212) and the C terminal peptide 390–398, containing two lysines, at least one of which is involved in DNA binding interaction. Replacement of the lysines 210–212 by glutamates or threonines resulted in the complete loss of DNA binding activity. Partial DNA binding activity was retained upon replacement of only one or two of the lysines with threonine. With respect to the C-terminal peptide, it was found that acetylation of K396, the most reactive lysine in rACT, was diminished in the presence of DNA, and replacement of the two lysines, K391 and K396, with threonine resulted in a protein with very little DNA binding capability. Accordingly, when producing and selecting recombinant ACT analogues, further modifications can be made at lysines 210–212 and in the C terminal peptide, 390–398 so that DNA binding of the inhibitor is modulated.

Using site-directed mutagenesis and chemical modification, a tri-lysine sequence (residues 210–212) falling within a solvent exposed loop and the C-terminal peptide containing two lysines (residues 391 and 396) have been found to be important for DNA binding. Mutation of residues 210–212 from lysines to either glutamates or threonines abolished DNA binding. As shown in Table 1, rACT was most strongly retained on the DNA cellulose column, requiring the highest KCl concentration for elution, while retention of the 210–212 analogs fell in the order KTK>TTK>TTT~EEE.

TABLE 1

| DNA CELLULOSE CHROMATOGRAPHY | |
|---|---|
| rACT | Salt Concentration (mM KCl) at center of eluting rACT peak |
| Wild Type | 300 - monomer |
|  | 400 - dimer |
| 210–212-KTK | 110 - monomer |
|  | 170 - dimer |
| 210–212-TTK | 70 - monomer and dimer (unresolved) |
| 210–212-TTT | None |
| 210–212-EEE | None |
| K391T/K396T | 20 - monomer only |

In accord with the DNA cellulose results, rACT and both KTK-rACT and TTK-rACT showed at least some binding to øX174-HaeIII fragments by gel shift assay, while TTT-rACT and EEE-rACT did not. In similar experiments using DNA-40 mer, cleaved ACT was found to bind DNA as strongly as intact rACT, demonstrating that binding does not depend on an intact active site loop of rACT (residues 345–365, Huber, R. and Carrell, R. W., *Biochemistry* 1989, 28, 8951), which is critical for the binding to and inhibition of chymotrypsin. The 40 residue double stranded DNA fragment used in these experiments, referred to as DNA-40 mer, was made up of residues corresponding to positions −56 to −90 of the ACT gene plus a 5' -AGGTT (SEQ ID NO: 10) used for radioactive and labeling, and has the sequence AGGTTTGG-GAAATGCCAGGACAACCAATGTTCTGTTCTA (SEQ ID NO: 11). No binding was observed to either (+) or (−) strands of DNA, demonstrating that binding is specific for dsDNA.

rACT was also demonstrated to bind to DNA-40 mer approximately one order of magnitude more tightly than either KTK-rACT or TTK-rACT in filter binding assays performed at low ionic strength. Neither TTT-rACT nor EEE-rACT showed any binding in the assay. rACT and rACT-chymotrypsin complex were found to bind to DNA with similar dissociation constants. Limited acetylation of rACT with acetic anhydride also led to a loss of DNA binding. Conversely, binding to DNA protected rACT from acetylation. A combination of CNBr digestion, peptide separation and peptide sequencing identified K396, two residues from the C-terminus, as the most reactive lysine in rACT toward acetylation. ACT binding to DNA protected K396 from acetylation.

The DNA binding activity of rACT has been found to be independent of its protease inhibitory activity. Thus, mutations or chemical modifications that decrease or abolish DNA binding have little or no effect on protease inhibitory activity, and, reciprocally, destruction of the active loop site necessary for protease inhibitory activity does not affect DNA binding. Further, complex formation with chymotrypsin has no effect on DNA binding and complex formation with DNA binding does not effect inhibitory activity of rACT. However, modulating the DNA binding capability of a serpin analog may result in altered physiological effects in vivo as compared with corresponding wild-type serpins. Such alterations are important in the development of these analogs as therapeutic agents (Rubin et al., *Biochemistry* 1994, 33, 7627).

It has been demonstrated that both the tri-lysine and C-terminal elements are necessary for DNA binding by ACT. Consistent with this demonstration is the fact that neither mouse contrapsin, which has a high degree of sequence identity (58%) with ACT, especially at the C terminus (Hill et al., *Nature* 1984, 311, 175; Suzuki et al., *J. Biochem.* 1990, 108, 344), but which lacks the lysine 210–212 loop, nor carbonic anhydrase, which contains a stretch of three lysines (residues 111–113), show demonstrable binding to DNA, as measured by DNA cellulose chromatography and gel shift assays. However, these same two DNA binding elements have been found in other known DNA binding proteins including, but not limited to, Bin 3, the cell cycle growth regulator p53, the accessory gene regulator protein (AGRP) and the 17 kDa protein in the DNAX 5' region (p17) indicating that the modifications described for rACT may also be applicable to other DNA binding proteins and serpins.

In the present invention, a method is provided for producing recombinant ACT analogues capable of effectively modulating their DNA binding capability. By modulating DNA binding capability, it is meant that the recombinant ACT analogues have a decreased binding affinity for DNA as compared to recombinant ACT. In this method, one or more amino acids comprising DNA binding elements of recombinant ACT are modified. In a preferred embodiment, the amino acid sequence of recombinant ACT is modified at DNA binding elements comprising either amino acids 210–212 of rACT or amino acids 390–398 of the C terminal peptide of rACT. Modifications to the amino acid sequence of recombinant ACT can comprise substitution or deletion of one or more amino acids in the sequence. In a preferred embodiment, the modification will consist of replacing one or more of lysine residues 210–212 with different amino acids such as, but not limited to, glutamates or threonines, or replacing residues K396 or K391 with an amino acid such as, but not limited to, threonine. In this embodiment, it is believed that the amino acids may be substituted with any amino acid with the exception of arginine and histidine.

In accordance with the teachings of the present invention rACT analogs having modified DNA binding elements are also provided. The analogs of the present invention have modulated DNA binding capability. In one embodiment, a composition of the present invention comprises recombinant ACT having a modified amino acid sequence at the DNA binding element comprising amino acids 210, 211 or 212. It is preferred that one or more of these amino acids be substituted with either a glutamate or threonine. In another embodiment, a composition of the present invention comprises recombinant ACT having a modified amino acid sequence at the DNA binding element comprising amino acids 390–398 of the C terminal peptide of recombinant ACT. It is preferred that one or both of residues K391 or K396 be modified to a threonine.

ACT is an acute phase protein; its serum concentration increases several fold (Katsunama et al., *Biochem. Biophys. Res. Commun.* 1980, 93, 552; Lindmark, B. E. and Eriksson, S. G., *Clin. Chim. Acta* 1985, 152, 261) in response to injury or infection. It is believed that its binding to DNA may provide a mechanism for the self regulation of ACT expression. Accordingly, compositions of the present invention are useful in diagnosing and treating patients with deficient amounts of a wild type ACT. Familial α1-Antichymotrypsin (ACT) deficiency, defined as plasma levels of less than 64% normal, has been studied in patients and their relatives with partial deficiency of less than 50% normal. Six out of eight ACT deficient individuals over 25 years of age had liver abnormalities, while three out of eight ACT deficient individuals had lung abnormalities. These manifestations varied from severe disease to subtle laboratory abnormalities and appear to be related to an abnormal expression of ACT resulting from a deletion of one or two alleles in the gene for ACT which causes uncontrolled activity of the protease Chtr. Eriksson et al., *Acta Med Scand* 1986, 220, 447. Two defective mutants of human α1-antichymotrypsin (ACT) gene have also been associated with chronic obstructive pulmonary disease (COPD). Poller, W. et al., *Genomics* 1993, 17, 740. A leucine 55-to-proline substitution causing a defective ACT allele was observed in a family with COPD in three subsequent generations. Another mutation, proline 229-to-alanine, was associated with ACT serum deficiency in four patients with a positive family history. In each of these mutations, the physiological manifestations related to the mutation can be alleviated by early diagnosis and treatment of the deficiency. Identification of mutations using well known PCR or RT-PCR techniques and correlation with recombinant ACT analogs of the present invention facilitates diagnosis of such conditions. In addition, the compositions of the invention are useful in treating these deficiencies.

The rACT compositions prepared in accordance with the teachings of the present invention can be used to supplement ACT in the treatment of diseases related to increased expression of proteases normally inhibited by ACT. Abnormal function of these proteases is associated with inflammation, emphysema, adult respiratory distress syndrome (ARDS) and rheumatoid arthritis. Serine proteases such as trypsin, chymotrypsin, elastase and enterokinase are involved in digestion. The abnormal function of these proteases is associated with pancreatitis. Serine proteases such as plasmin and plasminogen activator are associated with fibrinolysis. The abnormal function of these proteases is associated with tumor invasion. Serine proteases such as Factor IXI, Factor Xa, Factor XIa, Factor XIIa, Factor VIIa, thrombin, activated protein C and plasma kallikrein are involved in blood coagulation. The abnormal function of any of these proteases is associated with vascular clotting, cerebral infarction, and coronary infarction. Serine proteases such as Factor Clr, Factor Cls, Factor D, Factor B and C3 convertase are involved in complement activation. Abnormal function of these proteases is associated with rheumatoid arthritis and inflammation. Serine proteases such as tissue kallikrein and post proline cleaving enzymes are involved in hormone generation and degradation. The abnormal function of these proteases or their inhibitors is associated with inflammation. Serine proteases such as plasmin, plasminogen activator and acrosin are involved in ovulation and fertilization. The function of these proteases is associated with fertility control. ATP-dependent proteases are involved in protein turnover. Abnormalities associated with these proteases are involved in muscle degradation and fever.

The recombinant ACT analogues of the present invention are administered to a patient in an effective amount in the presence of a pharmaceutically acceptable carrier. By "effective amount" is meant a concentration of recombinant ACT which is capable of modulating an activity of a selected protease. This amount can be routinely determined by one of skill in the art in accordance with the weight, age and clinical condition of the patient. Suitable pharmaceutically acceptable carriers are well known in the art and are described, for example, in Gennaro, Alfonso, ed., *Remington's Pharmaceutical Sciences,* 18th edition, 1990, Mack Publishing Co., Easton, Pa., a standard reference text in this field. Suitable pharmaceutical carriers are selected in accordance with the intended route of administration and standard pharmaceutical practices. Such compositions can be administered by any suitable route including, but not limited to, intravenously, orally, intraperitoneally, intramuscularly, subcutaneously, topically, and by absorption through epithelial or mucocutaneous linings such as nasal, oral, vaginal, rectal, and gastrointestinal. The proportional ratio of active ingredient to pharmaceutical carrier will naturally depend on the chemical nature, solubility, and stability of the recombinant ACT analog. Compositions prepared in accordance with the disclosed invention may be administered either alone or in combination with other compounds, including but not limited to, other recombinant serine protease inhibitors, antibodies, toxins, and antisense oligonucleotides.

The following nonlimiting examples are provided to further illustrate the present invention.

EXAMPLES

EXAMPLE 1

Cloning and Expression of rACT Analogs

Site directed mutagenesis was carried out using the Amersham M13 in vitro mutagenesis kit (Amersham Corp., Arlington Heights, Ill.) and the synthetic primers shown below. Lys to Thr of Glu mutations are denoted in bold. GCACCATTACCCACTTTGTCTTGCTCAAGTAGAACC (SEQ ID NO: 1) for KTK-rACT, GCACCATTAC-CCACTCTTCCTCGCTCAAGTAGAACC (SEQ ID NO: 2) for EEE-rACT, GCACCATTACCCACGTTGTCTTGCT-CAAGTAGAACC (SEQ ID NO: 3) for TTK-rACT, and G C A C C A T T A C C C A C G T T G T C G T G C T - CAAGTAGAACC (SEQ ID NO: 4) for TTT-rACT. The altered genes were excised from double stranded M13 with EcoR1 and the overhanging ends made blunt by treatment with T4 polymerase. They were inserted into the expression vector pZM described by Rubin et al., *J. Biol. Chem.* 1990, 265, 1199 and Rubin et al., *Biochemistry* 1994, 33, 7627, to yield the 210–212 rACT mutants. The analog construction was confirmed by DNA sequencing. All of the 210–212 analogs and rACT have a Cys derived from exon I of the ACT gene at the N terminus: MGRDLCHPNSPL—(SEQ ID NO: 5).

The rACT-K391T/K396T double analog was constructed using PCR mediated mutagenesis. The N terminal primer (5' ATGGCTAGCAACAGCCCACTT 3' (SEQ ID NO: 6) contained an NheI site (italics) . The C terminal primer (5' TGGCTAGCCTAGGCTTGCGTGGGATTGGTGACTGT GCTCATGAAGAA3') (SEQ ID NO: 7) contained an NheI site (italics), a stop codon (underlined) and Lys to Thr mutations (bold) . The PCR product, representing the entire coding region, was cut with NheI, gel purified and inserted in the correct reading orientation in pZMs, a vector that does not have the N terminal Cys, to create the C terminus rACT analog, K391T/K396T-rACT. The N terminus of this analog is MASNSPL—(SEQ ID NO: 8). The analog construction was confirmed by DNA sequencing.

EXAMPLE 2

Purification of Wild-type rACT and Analogs rACT was purified as described by Rubin et al., *J. Biol. Chem.* 1990, 265, 1199 and Kilpatrick et al., *J. Immunol.* 1991, 146, 2388 using the successive chromatographic steps Fast Q followed by dsDNA cellulose. rACT and the 210–212 rACT analogs exist in solution as a mixture of monomer and dimer forms. Dimer formation results from disulfide bridge formation between cysteine residues located in the N-terminus. The K391T/K396T analog, lacking an N-terminal cysteine, exists only as a monomer. The KTK-rACT, TTK-rACT, and K391T/K396T-rACT analogs retained sufficient affinity for DNA that they could be purified to homogeneity by dsDNA cellulose chromatography. These analogs eluted at considerably lower KCl concentrations than wild-type rACT. The TTT-rACT and EEE-rACT analogs that displayed no binding to dsDNA cellulose were partially purified by Mono Q FPLC chromatography. Following Fast Q chromatography (Rubin et al., *J. Biol. Chem.* 1990, 265, 1199), these crude ACT analogs, containing approximately 10 mg total protein, were dialyzed against TK buffer, filtered by centrifugation through a 0.2 μm filter unit (Rainin Instrument Co., Woburn, Me.) and loaded onto a Mono Q HR 5/5 column (1 ml, Pharmacia Biotech Inc., Piscataway, N.J.) pre-equilibrate with TK buffer containing 50 mM Tris-HCl (pH 7.9) and 50 mM KCl . Chromatography was carried out with a 30 minute linear gradient 50 mM KCl to 350 mM KCl in 50 mM Tris-HCL (pH 7.9) followed by a 20 minute isocratic elution with the final buffer of the linear gradient. The flow rate was maintained a 1 ml/minute. Both ACT analogs eluted between 250–350 KCl.

By PAGE analysis it was shown that rACT and the three analogs (KTK, TTK, and K391T/K396T) displaying some retention on DNA cellulose were purified to near homogeneity. The TTT and EEE analogs were only approximately 50% pure following Mono Q chromatography, as estimated by titration inhibition of a standard chymotrypsin solution.

EXAMPLE 3

Preparation of Cleaved rACT by Treatment With Human Neutrophil Elastase (HNE)

Cleavage was carried out at an I/E ratio of 20. HNE concentration was determined by the catalysis of N-methoxysuccinylAAPV-p-nitroanilide (1 mM) hydrolysis (0.1M HEPES, pH 7.5, 0.5 NaCl, 25° C.), using change in absorbance of the sample at 410 nm and a specific activity of 0.0–53 absorbance units/min/pmol/ml, a value based upon titration of HNE with standardized α1-protease inhibitor. HNE (0.22 μM) was added to ACT (4.4 μM) in 0.1M Tris HCl, pH 8.3, containing 0.025% Triton X-100 and incubated at 25° C. for one hour. The cleavage reaction was stopped by the addition of PMSF to a final concentration of 2 mM. Full cleavage was verified by SDS-PAGE analysis (Schecter et al., *J. Biol. Chem.* 1993, 268, 23626). rACT is cleaved by HNE in the active loop region at positions P1—P1', P3–P4, and P5–P6 (Rubin et al., *Biochemistry 1994, 33, 7627*).

EXAMPLE 4

Gel Shift Assays

Gel shift assays of rACT and rACT analogs bound to double-stranded and single-stranded DNA were conducted in accordance with procedures described by Garner, M. and Revzin, A. *Nucleic Acids Res.* 1981, 9, 3047 and Maniatis et al. *"Molecular Cloning: A Laboratory Manual"*, 1982, Cold Spring Harbor Laboratory Press, Cold Spring Harbor, N.Y. Specifically, rACT (0 to 400 ng) was incubated with DNA (100 to 200 ng) in TE buffer (50 mM Tris-Cl (pH 7.9) and 1 mM EDTA) for 20 minutes at room temperature in a final volume of 20 µl, then electrophoresed on 2% agarose gels. Detection was by ethidium bromide (Sigma Chemical Company, St. Louis, Mo.) staining. For rACT analogs bound to double-stranded and single-stranded DNA, DNA was end-labeled with α-[$^{32}$P] CTP (Amersham Corp., Arlington Heights, Ill.) using Klenow fragment (New England Biolabs Inc., Beverly, Ma.). Approximately 0.3 ng of $^{32}$P-labeled DNA was incubated with ACT (0–15 µg) in TE buffer in a final volume of 15 µl for 20 minutes at room temperature. Samples were electrophoresed on 10% polyacrylamide gels in TBE buffer (50 mM Tris-borate (pH 8.3), 1 mM EDTA) and DNA-containing bands were detected by autoradiography.

EXAMPLE 5

Filter Binding Assays

Filter binding assays were performed using Schleicher and Schuell nitrocellulose filter (0.45 µM), (Keene, N.H.) and a 96 well suction manifold (V&P Scientific Inc., San Diego, Calif.). Standard assays were performed in DNA binding buffer (10 mM Tris-Cl (pH 7.5), 5 mM EDTA, 2 mM $CaCl_2$, 5% DMSO, and 0.1 mg/ml BSA (Promega Corp., Madison, Wis.) containing the appropriate concentration of KCl. Prior to use, filter were presoaked with this buffer, minus the BSA and DMSO. Reaction mixtures containing DNA binding buffer (70 µl), DNA (0.2 ng), and rACT or rACT analogs (0–7.5 µg) were incubated for 1 hour at room temperature and then filtered. The filters were washed with two 0.5 ml portions of DNA binding buffer at 4° C., dried, and counted in Scintiverse II cocktail (Fisher Scientific, Pittsburgh, Pa.) using a Beckman LS 7500 scintillation counter (Beckman Instruments, Fullerton, Calif.). DNA-40mer concentration was calculated assuming a molecular weight of 26,400.

EXAMPLE 6

Acetylation

Acetylation of rACT and of the rACT/DNA-40mer complex was carried out by initially reacting sample with limiting amounts of $^3$H-acetic anhydride followed by further reaction with unlabeled acetic anhydride under conditions producing more complete acetylation of available sites on rACT. The first acetylation step was carried out by adding 0.4 to 2.0 µmoles of $^3$H-acetic anhydride (50 mCi/mmole, Amersham Corp., Arlington Heights, Ill.) to 1 ml of 10.5 µM rACT in the absence or presence of 12.5 µM DNA-40 mer in 50 mM NaPi buffer (pH 8.15). For reactions carried out in the presence of DNA-40mer, rACT was preincubated with DNA-40 mer for 20 minutes prior to acetic anhydride addition. Under these conditions, approximately 95% of total rACT in solution is present as rACT/DNA-40 mer complex. The reaction was allowed to proceed for 5 minutes at room temperature, after which it was quenched by addition of 1.5 µl of 3.8 M $NH_2OH$. Following quenching, the rACT/DNA-40 mer complex was dissociated by addition of an equal volume of 2X TAU buffer (200 mM $NH_4Cl$, 5 M urea, 20 mM Tris-HCl (pH 7.9)) and heating at 40° C. for 20 minutes. DNA-40 mer was removed from the partly acetylated rACT by application of the dissociated complex to a DE-52 column (2 ml, pre-equilibrated with 5 M urea, 20 mM Tris-HCl (pH 7.9) and elution with TAU buffer. rACT was eluted within 4 ml while DNA-40 mer was retained. The rACT sample that was acetylated in the absence of DNA-40 mer was treated in exactly the same manner. Both rACT samples were dialyzed against 50 mM NaPi (pH 8.15) and concentrated by vacuum centrifugation (Savant Instruments Inc., Farmingdale, N.Y.) to approximately 10 µM in a volume of 0.96 ml. Unlabeled acetic anhydride (2.5 µmole portions) was then added every 5 minutes at room temperature to a total of 20 µmole, with a concomitant decrease in pH to 7.0. The samples were then dialyzed against 50 mM NaPi (pH 8.15), subject to another round of reaction with unlabeled acetic anhydride as described, and dialyzed in a Pierce Microdialyser against 100 mM Tris-HCl (pH 7.9). These acetylation conditions have been shown to result in a stoichiometry of 26 acetyl groups/rACT. There are a total of 26 Lys residues/rACT (Chandra et al., *Biochemistry* 1983, 22, 5055; Rubin et al. *J. Biol. Chem.* 1990, 265, 1199).

EXAMPLE 7

CNBr Cleavage of Acetylated rACT

ACT acetylated in the absence or presence of DNA-40 mer was cleaved with CNBr in accordance with the procedure described by Gross, E. and Wiktop, B., *J. Biol. Chem.* 1962, 237, 1856. In a typical reaction, about 500 µg (0.011 µmoles) rACT dissolved in 100 mM Tris-Cl (pH 7.9) was lyophilized, the resulting solid was dissolved in 70% formic acid (500 µl), CNBr (5 mg, 60 µmoles) was added and incubation was continued for 16 hours under $N_2$ at room temperature. The solution was then concentrated to dryness over NaOH pellets in a vacuum desiccator. Tricine-SDS-PAGE analyses of CNBr-generated peptides were performed in accordance with procedures described by Schagger, H. and von Jagow, G., *Anal. Biochem.* 1987, 166, 368. Peptides were also separated by RP-HPLC and by microbore capillary columns. Quantitative estimation of eluted peptides was obtained by $A_{214nm}$ absorbance in accordance with procedures described by Buck et al., *Anal. Biochem.* 1989, 182, 295. The product of peak area and flow rate was determined for elution of a known amount of standard peptide, N-acetyl LTDADF (SEQ ID NO: 9). This value was then used to calculate the amount of eluted, specifically acetylated peptide derived from rACT from the product of its peak area and flow rate.

EXAMPLE 8

Peptide Sequencing

Purified differentially labeled peptide was subjected to Edman sequencing on an ABI Model 473A sequencer (Applied Biosystems, Inc., Foster City, Calif.). The radioactivity in aliquots taken following each Edman cycle was determined in a Beckman LS 1801 counter (Beckman Instrument, Fullerton, Calif.).

What is claimed is:

1. A method of producing a recombinant α-1 antichymotrypsin analog comprising a modification of at least one of amino acids 210, 211, or 212 of recombinant α-1-antichymotrypsin or at least one of amino acids 390–398 in a C terminal peptide of recombinant α-1-antichymotrypsin so that the DNA binding capability of the recombinant α-1-antichymotrypsin analog is decreased, said method comprising:

(a) mutating a gene encoding α-1 antichymotrypsin so that the α-1 antichymotrypsin is modified at at least one of amino acids 210, 211, or 212 of recombinant α-1-antichymotrypsin or at least one of amino acids 390–398 in a C terminal peptide;

(b) inserting the mutated gene into an expression vector; and (c) introducing the expression vector into a cell line capable of expressing the vector so that the mutated gene is expressed and a recombinant α-1-antichymotrypsin analog is produced.

2. A recombinant α-1-antichymotrypsin molecule comprising recombinant α-1-antichymotrypsin having a modified DNA binding element comprising a modification of at least one of amino acids 210, 211 or 212 of recombinant ACT or a modification of at least one of amino acids 390–398 of a C terminal peptide of recombinant ACT.

* * * * *